United States Patent [19]
Roth et al.

[11] Patent Number: 5,192,439
[45] Date of Patent: Mar. 9, 1993

[54] BLOOD COLLECTION RESERVOIR AND FILTER DEVICE

[75] Inventors: Gary L. Roth, Elizabeth; William D. Zillmann, Broomfield, both of Colo.

[73] Assignee: Electromedics, Inc., Englewood, Colo.

[21] Appl. No.: 829,691

[22] Filed: Feb. 3, 1992

[51] Int. Cl.⁵ .................. B01D 29/11; B01D 29/27
[52] U.S. Cl. ........................ 210/485; 128/DIG. 3; 210/94; 210/416.1; 210/452; 210/454; 210/456; 422/101; 422/102; 604/4; 604/319; 604/403
[58] Field of Search ............ 210/94, 451, 452, 453, 210/454, 456, 457, 484, 485, 248, 416.1; 422/44, 101, 102; 604/4, 317, 318, 319, 403; 128/DIG. 3

[56] References Cited

U.S. PATENT DOCUMENTS

| | | | |
|---|---|---|---|
| 4,157,965 | 6/1979 | Raible | 210/446 |
| 4,164,468 | 8/1979 | Raible | 210/438 |
| 4,243,531 | 1/1981 | Crockett et al. | 210/456 |
| 4,664,682 | 5/1987 | Monzen | 210/436 |
| 4,705,497 | 11/1987 | Shitaokoshi et al. | 604/4 |
| 4,737,139 | 4/1988 | Zupkas et al. | 210/256 |
| 5,024,613 | 6/1991 | Vasconcellos et al. | 604/4 |
| 5,087,250 | 2/1992 | Lichte et al. | 604/319 |
| 5,120,302 | 6/1992 | Vescovini et al. | 604/4 |
| 5,127,900 | 7/1992 | Schickling et al. | 604/4 |

*Primary Examiner*—Robert A. Dawson
*Assistant Examiner*—Sun Uk Kim
*Attorney, Agent, or Firm*—Gary M. Polumbus

[57] ABSTRACT

A blood collection reservoir and filter device includes a generally cylindrical housing and an internal filter medium with the filter medium being retained in spaced relationship from the side wall of the housing so that blood can pass through the filter in a non-traumatized manner and flow smoothly onto a dispersion plate for cascading delivery to the internal surface of the side wall of the housing where it can flow in a non-traumatic manner to an outlet in the bottom wall of the housing. The filter medium includes a defoaming filter layer and a particulate filter layer so that blood removed from a surgical wound can be defoamed and filtered within the device. The filter is elevated within the housing to provide a relatively large temporary storage area where blood can be retained in non-contact with the filter.

14 Claims, 4 Drawing Sheets

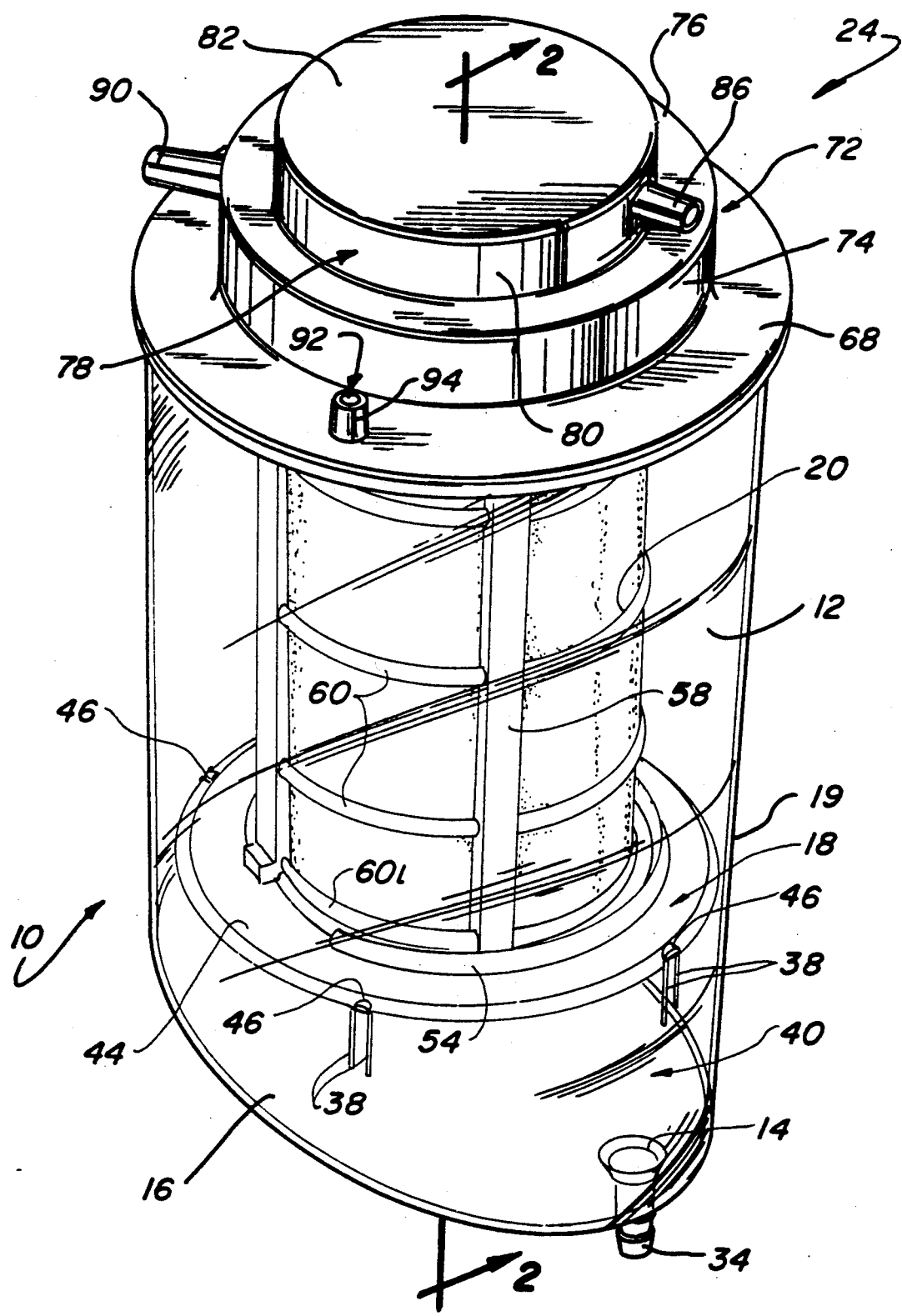
Fig_1

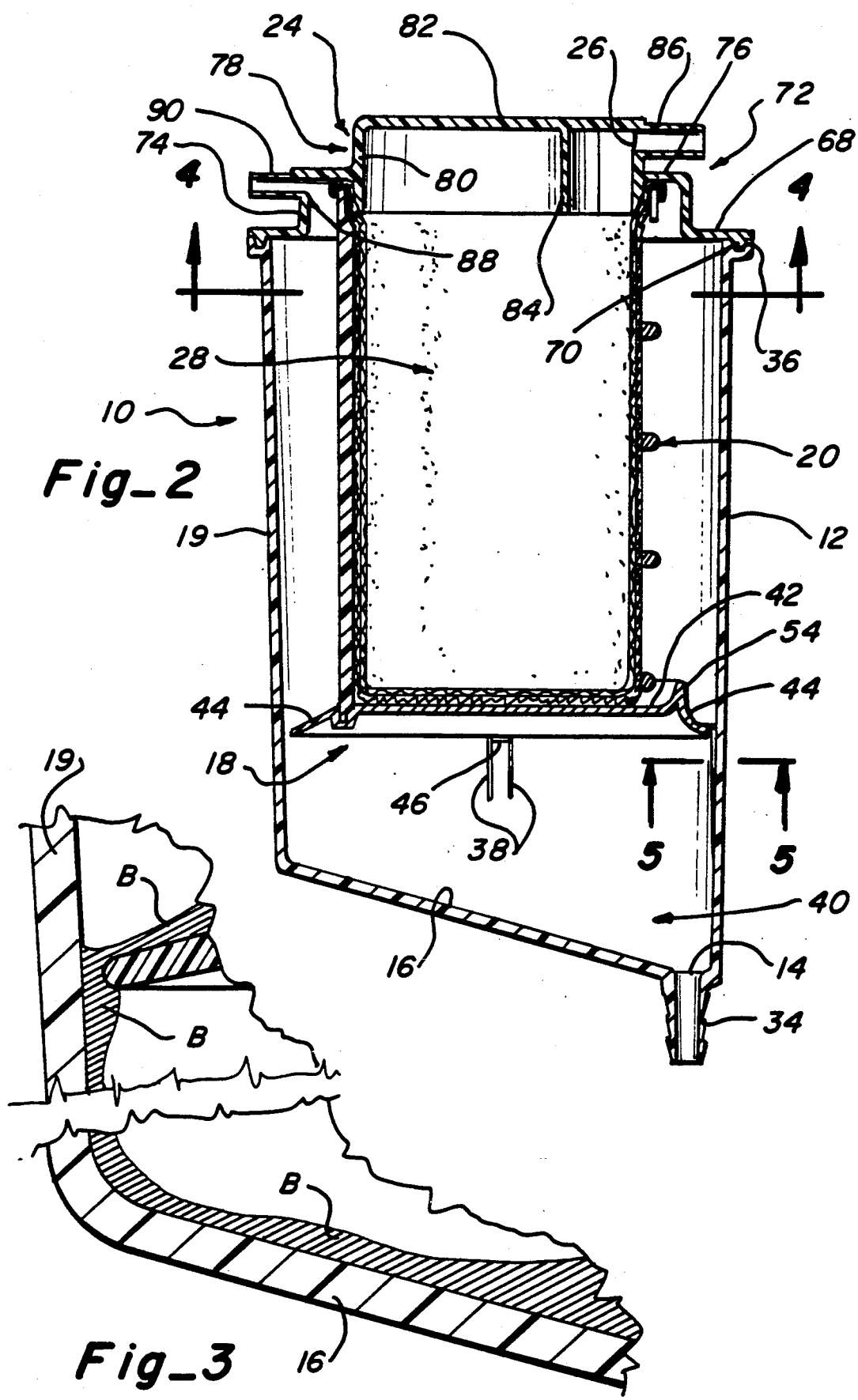

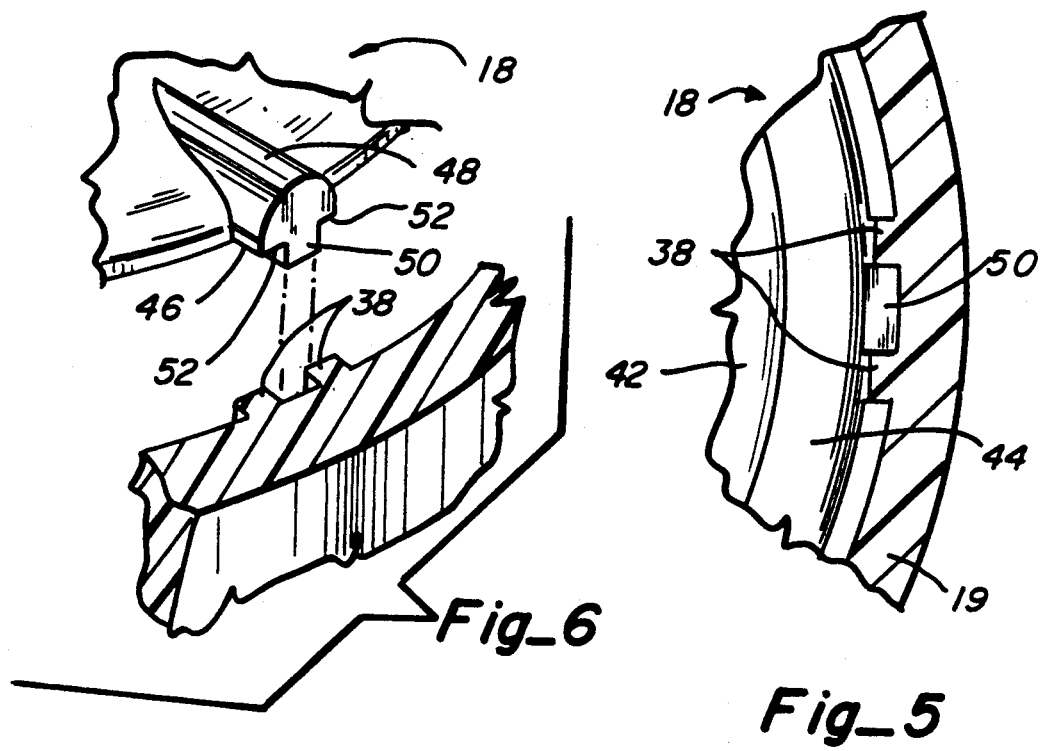
Fig_6
Fig_5
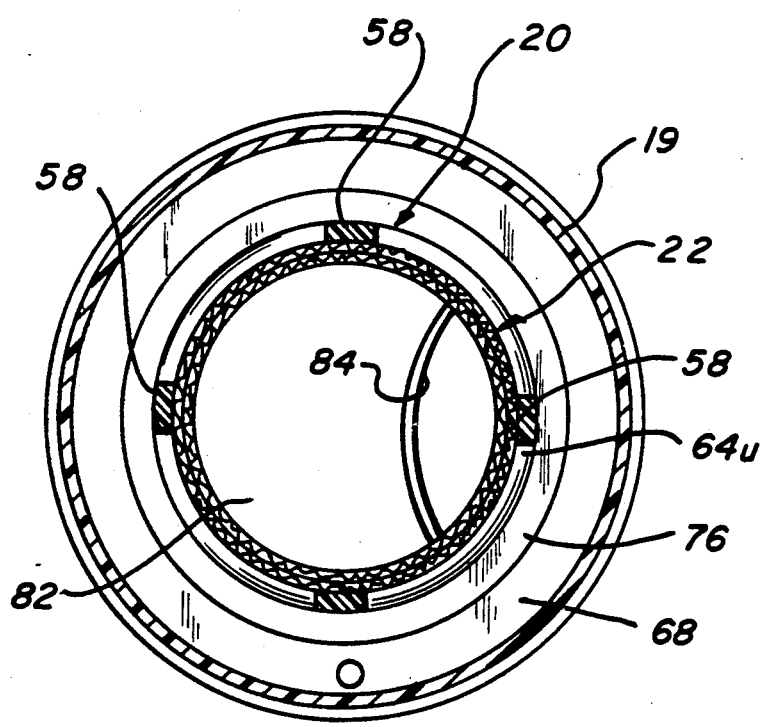
Fig_4

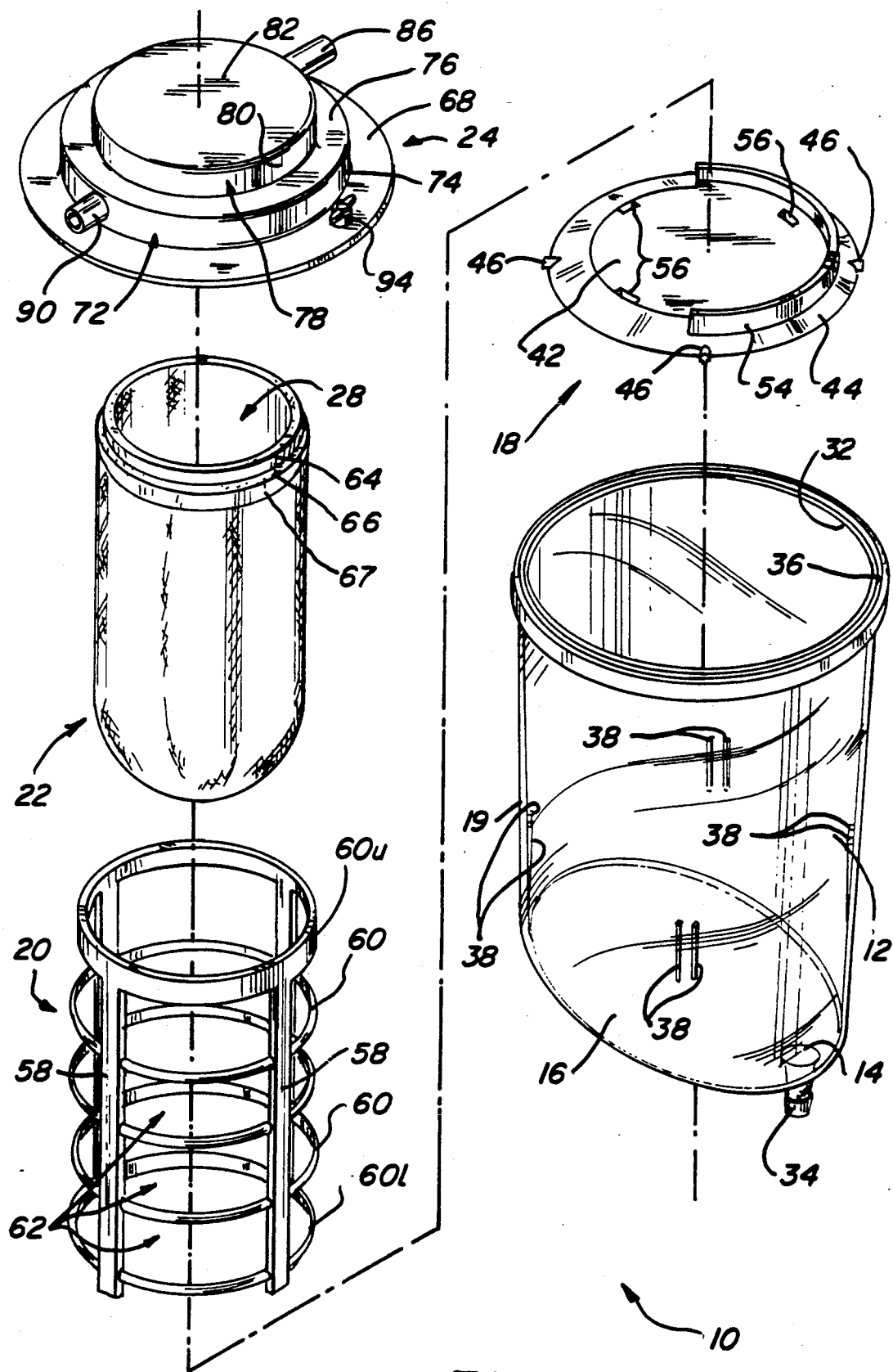
Fig_7

BLOOD COLLECTION RESERVOIR AND FILTER DEVICE

BACKGROUND OF THE INVENTION

1. Field of the Invention

The present invention relates generally to blood handling equipment and more particularly to a blood reservoir and filter device wherein blood removed from the human body during surgical procedures can be filtered and temporarily stored before being further treated and returned to the patient.

2. Description of the Prior Art

In recent years, it has become more desirable and possible to recapture and treat blood that was previously lost during surgical procedures. The advent of equipment for this purpose has taken on new significance due to the risks inherent in normal blood transfusions which were previously necessary to replace blood that was lost or discarded during surgery. The risks of blood transfusions obviously include the exposure to A.I.D.S. and other such diseases which may be carried by the blood of a third-party source of the blood.

Blood removed from a surgical wound is usually withdrawn with a suitable vacuum source, but since the blood is typically contaminated with gas bubbles, tissues fragments, surgical debris and the like, it is necessary to filter and treat the blood before it is returned to the surgical patient. It is also desirable that the blood, while outside the human body, be carefully handled so as not to traumatize and/or otherwise damage the blood before its reinfusion into the patient.

Blood can be damaged through trauma if it is allowed to abruptly impact hard surfaces, and for this reason, filter devices for receiving such blood have been very carefully designed. For example, U.S. Pat. No. 4,737,139 issued to Zupkas et al. shows that it is desirable to allow incoming blood to flow smoothly over an entry cone having a rounded upper tip so that the blood does not fall a significant distance onto a hard surface where it might be damaged. It is also known, as evidenced by the patents to Raible Nos. 4,157,965 and 4,164,468, to allow the blood to flow smoothly over a conical surface as it passes through a filter medium again to minimize the exposure to trauma. A problem with filter devices of the type disclosed in the Raible patents, however, resides in the fact that, after the blood has passed through the filter and flowed smoothly across a conical surface, it is allowed to pass through notches in the surface from where the blood falls onto a hard bottom wall of the device. The Raible devices minimize the trauma by reducing the distance through which the blood falls onto the hard surface at the bottom of the device, but this arrangement necessitates a small receiving and storing area beneath the filter medium.

Since blood sometimes needs to be retained in a filter device until it can be further processed for reinfusion, it is desirable that the holding space within the filter device be of a sufficient size to retain the filtered blood in non-engagement with the filter medium. This is important due to the fact that typically the filter medium is treated with a silicone material to facilitate defoaming of the blood and prolonged exposure to the silicone material can contaminate the blood. As will be appreciated, if the storage space within the filter device is enlarged to accommodate a significant volume of blood in non-contact with the filter medium, devices of the type disclosed in the Raible patents, wherein the blood is allowed to drop from a conical surface to the bottom of the filter, become undesirable as the distance the blood falls is enlarged thereby exposing it to trauma.

U.S. Pat. No. 4,664,682 issued to Monzen discloses a blood filter device which deals with this particular problem by elevating the filter material within an outer housing and allowing the blood to flow downwardly from the filter medium along an inverted conical surface toward the bottom of the housing where the blood flow is transferred to a second upright conical surface before being removed from the housing. In other words, by transferring the blood between cooperating conical surfaces, the device enables the blood to pass through a relatively large storage area without allowing the blood to fall a great distance into contact with a hard surface where it might be traumatized.

Another problem with most prior art filters is that the filter medium, which is typically cylindrical in configuration to define an enclosed chamber into which blood is introduced, is suspended or otherwise secured to the outside of a supporting filter cage. The cage is made of a hard material so that blood that is allowed to engage the cage, including a hard bottom wall thereof, can be traumatized unless it is carefully handled by passage across conical dispersion surfaces such as of the type found in the previously mentioned patent to Zupkas et al.

The provision of such conical flow plates of the type found in the Monzen patent, add expense and complexity to the filters and therefore are not entirely satisfactory for that reason. Without the conical flow plates, however, the blood can be easily damaged by impact with relatively hard surfaces within the device.

U.S. Pat. No. 4,243,531 issued to Crockett et al. deals with the cage problem by providing a solid mass of filter material on the inside of a perforated cage so that the blood engages the filter immediately upon entry into the device and therefore does not fall directly upon the relatively hard cage material. After passing through the filter medium and subsequently the perforated wall of the cage, however, the blood must flow along the relatively rough outer surface of the cage where it continuously encounters and engages the walls of the numerous perforations in the cage. This engagement, of course, again exposes the blood to possible trauma which it is desirable to avoid.

It will be appreciated from the afore-noted description of the prior art that, while the industry is aware of the problems which are desirable to avoid when treating and handling blood in a reservoir and filtering device, there are shortcomings in each of the prior art devices which negatively impact the device either from an operation or economic standpoint. It is to overcome these shortcomings in the prior art that the present invention has been developed.

SUMMARY OF THE INVENTION

The blood reservoir and filter device of the present invention includes an outer generally cylindrical housing having an inclined bottom wall with means on the side wall of the housing for supporting a filter cage at an elevated position within the housing. The cage in turn supports internally a filter medium which defines a chamber into which blood is admitted through an inlet provided in the top of the reservoir. A partially tapered dispersion plate is positioned immediately beneath the filter medium in a position to receive filtered blood and allow it to flow radially outwardly toward the internal surface of the side wall of the housing. Blood on the dispersion plate is smoothly transferred onto the internal surface of the side wall of the housing so that it can cascade and flow downwardly onto the bottom wall of the housing for removal through an outlet provided at the lowest point of the bottom wall.

The device therefore permits blood to be introduced therein in a manner such that it falls onto the relatively soft filter medium through which it passes downwardly onto a dispersion plate in a manner so as to avoid traumatic contact with relatively hard surfaces. It will be appreciated that the need and added cost of an inlet dispersion conical surface are avoided due to the fact that the blood on entry into the device falls on a relatively soft surface. Since the cage which supports the filter medium is positioned on the outside of the filter medium, blood introduced to the device can only encounter the cage after having passed slowly through the filter medium so as to minimize any trauma that may be caused by engagement of the blood with the cage.

Further, since the blood emanating from the filter medium flows smoothly across the dispersion plate and cascades onto the internal surface of the side wall of the housing, it is not allowed to drop through space onto hard surfaces. The dispersion plate further includes an arcuate wall or dam which extends a significant distance therearound so that blood can be channeled to one side of the dispersion plate for delivery to the side of the housing which is opposite the side on which the outlet from the housing is positioned. In this manner, the blood flows down the shortest side of the housing in a smooth laminar flow before being transferred onto the bottom wall of the housing again to minimize any possibility of trauma to the blood.

The dispersion plate which in turn supports the cage in which the filter medium is disposed is supported within the housing by supports that are formed on the internal surface of the side wall of the housing. The supports are disposed at an elevation to provide a significant reservoir space beneath the filter in which the blood can accumulate in non-engagement with the filter medium.

It will be appreciated from the above and from the detailed description to follow that the blood collection reservoir and filter device of the present invention has been designed to handle blood in a non-traumatic manner while desirably filtering air bubbles and other debris out of the blood. The device is further economical to manufacture and therefore provides a highly desirable blood collection reservoir and filter device for the medical industry.

Other aspects, features and details of the present invention can be more completely understood by reference to the following detailed description of a preferred embodiment, taken in conjunction with the drawings, and from the appended claims.

DESCRIPTION OF THE DRAWINGS

FIG. 1 is an isometric view of the blood collection reservoir and filter device of the present invention.

FIG. 2 is a reduced section taken along line 2—2 of FIG. 1.

FIG. 3 is an enlarged fragmentary section taken through a lower portion of the housing of FIG. 1 illustrating the flow of blood across the dispersion plate and cascading onto the internal surface of the side wall and flowing downwardly to the bottom wall of the housing.

FIG. 4 is a section taken along line 4—4 of FIG. 2.

FIG. 5 is an enlarged fragmentary section taken along line 5—5 of FIG. 2.

FIG. 6 is a fragmentary isometric view illustrating the interconnection between the dispersion plate and the side wall of the housing of the device shown in FIG. 1.

FIG. 7 is an exploded isometric view of the device of FIG. 1.

DESCRIPTION OF THE PREFERRED EMBODIMENT

The blood collection reservoir and filter device lo of the present invention is probably best seen in FIGS. 1 and 7 to include a generally cylindrical housing 12 having an outlet port 14 formed in a bottom wall 16 thereof, a dispersion plate 18 supported in an elevated position on the internal surface of the side wall 19 of the housing, a filter cage 20 supported on the dispersion plate in which a filter medium 22 is disposed, and a top 24 which is hermetically sealed to the housing and in which an inlet port 26 to the device is formed. The inlet is in communication with a chamber 28 defined by the filter medium so that blood introduced to the device through the inlet 26 passes through the filter medium 22, across the dispersion plate 18 and cascades downwardly onto the internal surface of the side wall of the housing 12 before being removed through the outlet 14 in the bottom wall of the housing.

The housing 12 is open at its upper end 32 and is of generally cylindrical configuration even though the side wall 19 thereof converges slightly downwardly. The bottom wall 16 is integral with the side wall and is inclined relative to the longitudinal axis of the housing. The outlet 14 is positioned in the bottom wall at its lowest point to receive blood flowing across the bottom wall that is channeled into the outlet. An attachment neck 34 projects downwardly from the bottom wall in communication with the outlet so that a removal hose or the like (not shown) can be removably attached thereto.

Due to the inclination of the bottom wall, the length of the side wall varies around the circumference of the housing. For purposes of the present disclosure, reference will be made to the short side or the long side of the side wall with the long side being that portion of the side wall adjacent to the outlet 14 and the short side being that portion which is diametrically opposite the long side.

The opening at the upper end 32 of the housing has a circular channel 36 therearound to facilitate attachment of the top 24 to the housing. The housing is preferably made of a transparent, rigid plastic material which is non-contaminous to the blood processed therein. Circumferentially spaced around the internal surface of the side wall 19 at 90° intervals are pairs of spaced vertical support ribs 38 adapted to cooperate with the dispersion plate 18 in supporting and spacing the dispersion plate in an elevated position within the housing. The top edges of the support ribs are located at approximately two-thirds the distance from the top of the housing to the bottom along the long side of the housing. In this manner, a space 40 is defined within the housing and beneath the dispersion plate that is at least 1,000 ml in volume.

The dispersion plate 18 is also preferably made of a transparent, rigid, plastic material and has a central circular disk-like body 42 from which an outwardly and downwardly inclined frusto-conical ring 44 integrally projects. At equally spaced 90° intervals around the dispersion plate, four radially projecting tabs 46 are formed in the edge of the frusto-conical ring 44 which are adapted to cooperate with the support ribs 38 in properly positioning and supporting the dispersion plate within the housing. The tabs 46 are best illustrated in FIG. 6 to define in cross-section a semi-cylindrical body 48 having a rectangular central projection 50 from the bottom surface thereof. The rectangular projection is adapted to be received between associated support ribs 38 on the internal surface of the side wall of the housing so that shoulders 52 defined between the rectangular projection 50 and the semi-cylindrical body 48 will rest on the top edges of the support ribs to properly and positively position the dispersion plate within the housing. It will be appreciated that the tabs project outwardly from the outer edge of the frusto-conical ring 44 a slight distance, and it is also to be realized that the outer terminal ends of the tabs are adapted to engage the inner surface of the side wall 19 of the housing 12 so that the outer perimeter or edge of the frusto-conical ring 44 is spaced a slight distance from the inner surface of the side wall of the housing for a purpose to become more clear later. The spacing between the outer edge of the frusto-conical ring 44 and the internal surface of the side wall 19 varies slightly from approximately 0.045 inches±0.004 at the short side of the housing to approximately 0.055 inches±0.004 at the long side of the housing.

A semi-cylindrical wall or dam 54 projects vertically upwardly from the dispersion plate 18 along the frusto-conical ring portion 44 thereof, and the dispersion plate is positioned within the housing so that the longitudinal center of the wall 54 is aligned with the long side of the housing whereby the longitudinal center of the wall is vertically aligned with the outlet 14 from the housing. The larger spacing at the long side of the housing is provided to accommodate a larger flow of blood in circumstances where the rate of flow of blood through the filter medium causes the blood to overflow the wall 54. It also facilitates venting at lower blood flow rates. The spacing at all points along the perimeter of the ring, however, is such as to permit a smooth cascading transition of the flow of the blood from the frusto-conical ring 44 to the side wall of the housing.

Four substantially rectangular recesses 56 are also provided in the upper surface of the disk-like body 42 of the dispersion plate at 90° intervals along the outer peripheral edge thereof with the recesses adapted to cooperate with the filter cage 20 in supporting the cage within the housing.

The filter cage 20 is a generally cylindrical skeletal body having four vertical extending ribs 58 spaced at equal 90° intervals and five equally spaced circular horizontal ribs 60 which are integrally connected to the vertical ribs. In the preferred embodiment, the horizontal ribs are spaced in approximately 1½ inch intervals to define large substantially rectangular openings 62 in the side of the cage. The uppermost circular rib 60u has a slightly greater depth than the remaining circular ribs for structural integrity purposes. It should also be appreciated that the lowermost circular rib 60l is connected to the vertical ribs 58 at a slightly spaced location relatively to the lowermost end of the vertical ribs so that the vertical ribs, which are of substantially rectangular cross-section, can be seated in the rectangular recesses 56 provided in the main body of the dispersion plate. With the vertical ribs seated in the recesses, the lowermost circular rib 60l is slightly spaced from the top surface of the dispersion plate 18. The filter cage is also preferably made of a relatively transparent, rigid, plastic material so as to remain erect within the housing in a radially inwardly spaced position relative to the side wall 19 of the housing 12. The overall height of the filter cage is such that it extends beyond the open top 32 of the housing a short distance when supported by the dispersion plate.

The filter medium 22 may be of two or three layers with at least one layer being specifically adapted to defoam blood that has been deposited therein and at least another layer being adapted to filter particulate matter from the blood before it is removed from the device. The layers of filter material are identically configured in a generally cylindrical form having a closed bottom. In the three-layer filter medium illustrated, the defoaming filter layer 64 is positioned internally of the intermediate particulate filter layer 66 and an outermost cover layer 67 is also included. The overall length of the filter medium is such that the closed bottom rests upon the top surface of the disk-like main body 42 of the dispersion plate 18 and extends beyond and folds over the uppermost circular rib 60u on the filter cage 20. The enlarged size of the upper circular rib provides adequate strength for supporting the filter medium within the cage.

For purposes of example only, the three-layer filter medium of the type illustrated might have an inner layer 64 (FIG. 7) of Z-type reticulated polyester urethane foam as the defoaming filter layer. The intermediate layer material 66 is a non-woven, polyester material with the outer layer 67 being common circular knit polyester. All three filter materials are available from Lydall, Inc. of Hamptonville, N.C. The filter materials used for filtering blood in this type of application are well known in the field so that a more detailed description thereof is not felt necessary.

In a two-layer embodiment of the filter medium (not illustrated), both layers would be of Z-type reticulated polyester urethane foam with the inner layer having approximately 20 pores per inch for defoaming purposes and the outer layer having approximately 100 pores per inch to filter particulate materials.

The top 24 of the device has a circular horizontal flange 68 with a depending circular rib 70 (FIG. 2) along its periphery and a first raised cylindrical section 72 formed along the inner periphery of the flange 68. The first raised cylindrical section 72 has a cylindrical side wall 74 and ring-like top 76 so that a second cylindrical section 78 formed contiguous with the inner edge of the ring-like top 76 forms an upward projection from the ring-like top. The second section 78 has a cylindrical wall 80 that projects upwardly and downwardly from the ring-like top 76 of the first section and has a closed disk-shaped top wall 82. The diameter of the cylindrical wall 80 is slightly less than the diameter of the filter cage 20 so that the top 24, when positioned on the housing 12 of the device 10, permits the cylindrical wall 80 to project inwardly a slight distance into the filter cage to pinch the filter medium 22 between the filter cage and the cylindrical wall 80 to hold the filter in position within the filter cage.

An arcuate deflector wall 84 is formed on the bottom surface of the disk-shaped top wall 82 adjacent to the inlet port 26. The inlet port has a generally cylindrical radial projection 86 therefrom adapted to releasably receive an inlet hose (not shown). In this manner, blood can be introduced to the device 10 through the inlet port and be directed downwardly by the arcuate deflector wall 84 into the interior of the filter medium 22. On the opposite side of the top 24 from the inlet port 26, a second port 88 having a cylindrical extension 90 is formed in the cylindrical wall 74 of the first raised section. The extension 90 is adapted to releasably receive a vacuum line (not shown). The vacuum line, of course, is utilized to lower the pressure within the device 10 to draw blood thereinto and through the filter medium 22 before it is allowed to flow by gravity through the outlet 14 in the bottom wall of the housing. Still another port 92 is provided through the horizontal flange 68 on the top 24 with the port 92 having an upstanding neck 94 with a Luer-type connector so that medicinal treatments can be introduced to the device in a controlled manner. Treatments might include heparin or other anti-coagulant drugs.

The depending rib 70 on the top 24 of the device is adapted to be received in the channel 36 provided around the open upper end 32 of the housing. The rib 70 is hermetically sealed in the channel 36 in any conventional manner whereby a low pressure can be created within the device 10 when the various ports of the device are closed.

With the device 10 assembled in the manner previously described, the operation can be readily understood. A vacuum may be drawn or at least a low pressure condition established within the device through the vacuum port 88 so that blood entering the device through the inlet 26 is encouraged to flow into and through the filter medium 22 and subsequently through the outlet 14 from the device. Dirty blood entering the device is directed immediately into the internal chamber 28 defined by the filter medium. It will be appreciated that blood entering the chamber 28 is directed onto the relatively soft reticulated foam filter material 64 and thereby does not encounter harsh or other hard surfaces where it might be traumatized. Any air bubbles entrained within the blood entering the device are trapped within the filter medium by the reticulated foam filter layer 64 and particulate debris within the blood is filtered therefrom by the particulate, non-woven filter layer 66 as the remainder of the blood passes therethrough. As the blood emerges from the outer surface of the filter medium, it trickles downwardly along the outer wall of the filter medium and slowly across the circular ribs 60 of the filter cage before being softly deposited onto the frustoconical ring 44 of the dispersion plate 18. Any blood deposited along the side of the dispersion plate where the semi-cylindrical wall or dam 54 extends will be channeled by the wall or dam toward the opposite unimpeded side of the dispersion plate. As mentioned previously, this unimpeded side of the dispersion plate is adjacent to the short side of the housing side wall 19.

As best seen in FIG. 3, the small spacing between the outer periphery of the frusto-conical ring 44 and the inner surface of the side wall 19 of the housing permits the blood B to be transferred directly from the frustoconical ring in a cascading manner onto the internal surface of the side wall of the housing 12 along which it flows in laminar sheets downwardly due to the slightly inward taper of the side wall. The blood subsequently flows smoothly onto the bottom wall 16 of the device 10 and thereafter is channeled into the outlet 14 which is positioned at the lowest point of the housing. The blood is selectively removed from the device through the outlet for further processing and reinfusion in a conventional manner.

It is important to note that, with the arrangement of the present invention, a relatively large temporary storage space 40 is provided within the device 10 which is separated from the filter medium 22 so that filtered blood can accumulate in a region that is not exposed to the filter medium which frequently is silicone coated to defoam the blood. It is also important to note that the passage of blood through the device is accomplished in a non-traumatic manner by allowing the blood to interact only with relatively soft surfaces except where it flows smoothly across the harder surfaces of the dispersion plate and the internal surface of the side walls 19 of the housing 12. The blood is not allowed, however, to drop onto hard surfaces which might damage the cells in the blood.

Although the present invention has been described with a certain degree of particularity, it is understood that the present disclosure has been made by way of example, and changes in detail or structure may be made without departing from the spirit of the invention, as defined in the appended claims.

We claim:

1. A device for filtering and storing blood comprising in combination, a tubular housing having a vertical central axis, a continuous side wall extending substantially parallel to said axis, a top wall and a bottom wall, a tubular vertically extending cage supported within said housing in spaced relationship with said side wall, an outwardly flared and downwardly tapered ring operatively connected to a lower portion of said cage, said ring having an outer edge closely spaced from said side wall, a cylindrical filter medium confined to said cage and defining a chamber within said housing, an inlet to the interior of said housing in communication with said chamber for admitting blood to the chamber and an outlet from the bottom of said housing through which blood can be removed from the housing whereby blood entering said chamber must pass through said filter medium and onto said ring before flowing across the ring and cascading to an internal surface of the side wall of the housing where it flows downwardly along said side wall for removal through said outlet.

2. The device of claim 1 wherein said housing and said cage are of circular transverse cross-section.

3. The device of claim 2 wherein said bottom wall is inclined relative to said central axis and said outlet is positioned adjacent to said side wall at the lowest part of said housing.

4. The device of claim 3 further including a substantially vertical arcuate wall protruding upwardly from said ring, said wall extending less than the full distance around said ring and being adapted to divert the flow of blood across said ring.

5. The device of claim 4 wherein said side wall is discontinuous along the side of said housing opposite the location of said outlet.

6. The device of claim 1 further including a space in said housing beneath said chamber, said space being at least 1000 ml in size.

7. The device of claim 1 further including supports on said side wall of the housing, said supports operatively supporting said cage in an elevated position relative to the bottom wall of said housing.

8. The device of claim 7 further including a space in said housing beneath said chamber, said space being at least 1000 ml in size.

9. The device of claim 1 wherein said filter medium is disposed internally of said cage.

10. The device of claim 9 wherein said cage includes a plurality of interconnected vertical and circumferential ribs defining a gridwork within which said filter medium is confined.

11. The device of claim 10 wherein said cage has four equally spaced vertical ribs.

12. The device of claim 10 wherein the circumferential ribs are spaced approximately 1½ inches from each other.

13. The device of claim 12 wherein said cage has four equally spaced vertical ribs.

14. A device for filtering and storing blood comprising in combination, a substantially cylindrical housing with a vertical central axis and having a slightly downwardly convergent side wall of circular cross-section and an inclined bottom wall, an outlet formed in the lowest portion of said housing, support means on the side wall, a ring supported by said support means in an elevated position relative to said bottom wall so as to define a space beneath said ring and within said housing of at least 1000 ml, said ring being of frusto-conical configuration and tapering radially outwardly and downwardly, a filter cage supported on said housing having a plurality of interconnected vertical ribs and horizontal circular ribs, a filter medium positioned within said cage defining an interior chamber, said filter medium having a substantially cylindrical side wall and a bottom wall, and a top hermetically sealed to said housing, said top having an inlet opening in communication with said interior chamber whereby blood introduced to said device will fall directly onto said filter medium, and a vacuum port in said device whereby the pressure within the device is selectively lowerable.

* * * * *